United States Patent
Persat

(10) Patent No.: US 10,478,220 B2
(45) Date of Patent: Nov. 19, 2019

(54) MEDICAL INSTRUMENT FOR IMPLANTING PINS

(71) Applicant: Caroline Persat, Geneva (CH)

(72) Inventor: Caroline Persat, Geneva (CH)

( * ) Notice: Subject to any disclaimer, the term of this patent is extended or adjusted under 35 U.S.C. 154(b) by 575 days.

(21) Appl. No.: 15/114,099

(22) PCT Filed: Jan. 29, 2015

(86) PCT No.: PCT/FR2015/050216
§ 371 (c)(1),
(2) Date: Jul. 26, 2016

(87) PCT Pub. No.: WO2015/114268
PCT Pub. Date: Aug. 6, 2015

(65) Prior Publication Data
US 2017/0000524 A1 Jan. 5, 2017

(30) Foreign Application Priority Data
Jan. 30, 2014 (FR) ..................... 14 00246

(51) Int. Cl.
| A61B 17/34 | (2006.01) |
| A61B 17/88 | (2006.01) |
| A61B 17/72 | (2006.01) |
| A61B 17/00 | (2006.01) |

(52) U.S. Cl.
CPC ...... *A61B 17/3468* (2013.01); *A61B 17/3472* (2013.01); *A61B 17/7233* (2013.01); *A61B 17/8872* (2013.01); *A61B 17/7208* (2013.01); *A61B 2017/0046* (2013.01)

(58) Field of Classification Search
CPC ............ A61B 17/3468; A61B 17/7208; A61B 17/3472; A61B 17/72; A61B 2017/90; A61B 17/3403
See application file for complete search history.

(56) References Cited

U.S. PATENT DOCUMENTS

| 6,007,519 A * | 12/1999 | Rosselli | A61M 25/0606 604/164.01 |
| 6,309,396 B1 | 10/2001 | Ritland | |
| 6,641,564 B1 * | 11/2003 | Kraus | A61B 17/3415 604/110 |
| 7,842,038 B2 * | 11/2010 | Haddock | A61B 17/3472 604/164.01 |
| 2007/0012816 A1 | 1/2007 | Kaup et al. | |

(Continued)

*Primary Examiner* — David W Bates
(74) *Attorney, Agent, or Firm* — Clark & Brody

(57) ABSTRACT

The invention relates to a medical instrument for putting pins (2) into place, the instrument comprising:
at least one rectilinear pin (2) presenting a determined length and a determined diameter;
an insertion trocar (5) comprising a guide sheath (6);
a guide (10) for a pin (2) the guide comprising a flexible tube (11) presenting an outside diameter less than the inside diameter of the sheath to enable it to be inserted in the sheath, the flexible tube (11) presenting between its distal end and its proximal end a length that is greater than the length of the pin; and
a positioner (13) for positioning a pin (2), the positioner comprising an obturator (14) possessing an outside diameter less than the inside diameter of the flexible tube (11) in order to enable it to be inserted in and to slide inside the flexible tube.

14 Claims, 6 Drawing Sheets

(56) References Cited

U.S. PATENT DOCUMENTS

| | | | |
|---|---|---|---|
| 2008/0033432 A1 | 2/2008 | McGraw et al. | |
| 2009/0149890 A1* | 6/2009 | Martin | A61B 17/1717 606/316 |
| 2013/0324997 A1 | 12/2013 | Pellegrino et al. | |

* cited by examiner

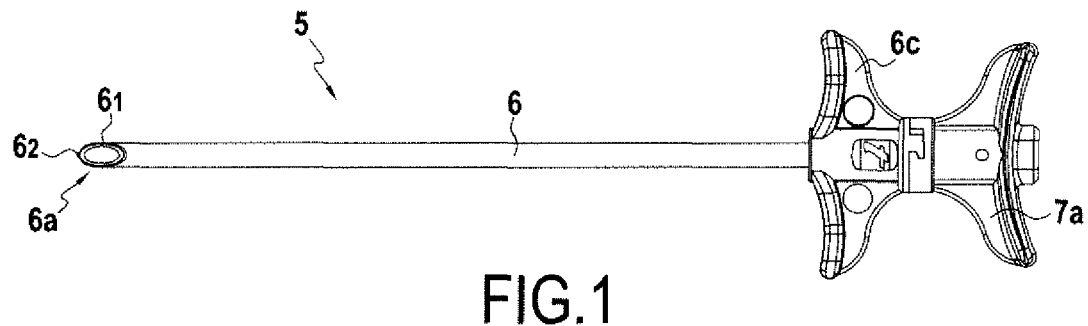
FIG.1
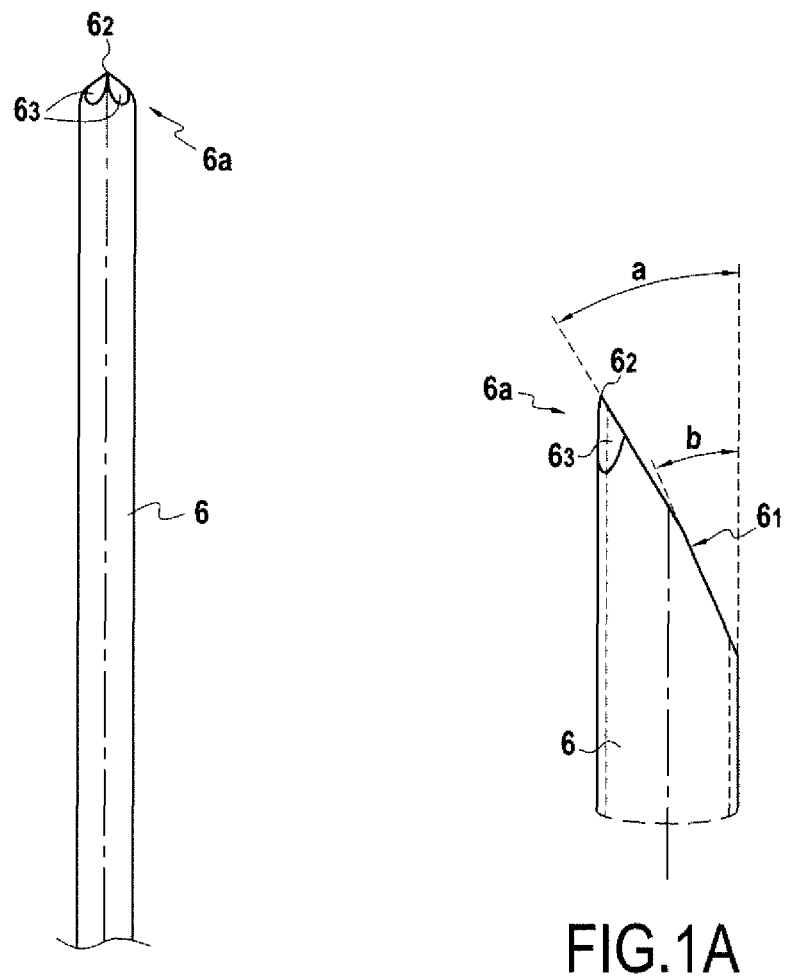
FIG.1A
FIG.1B

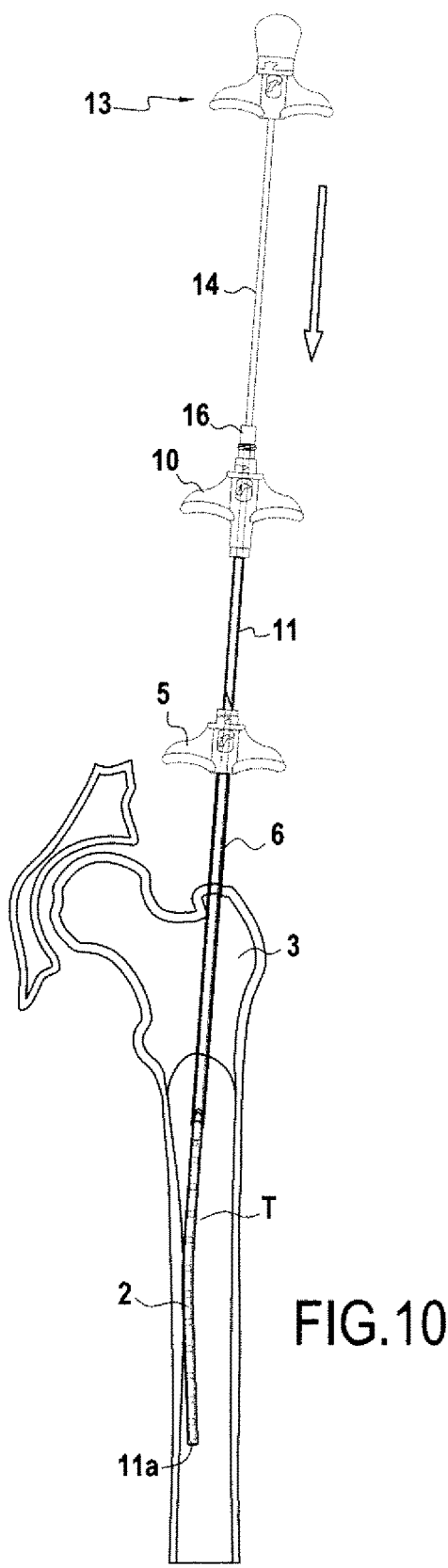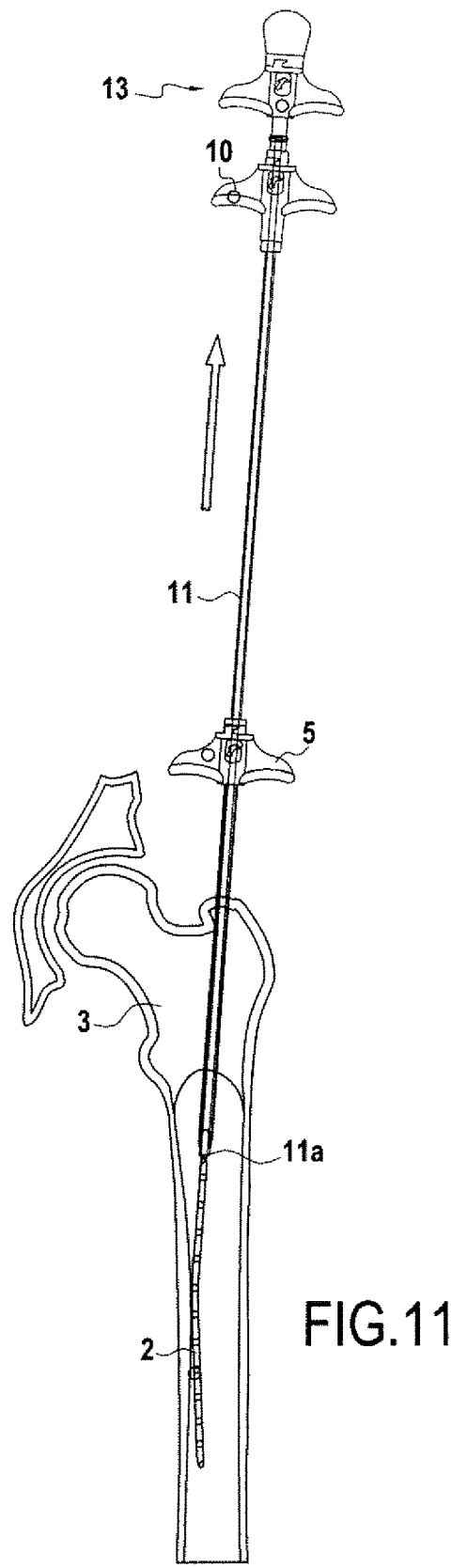

MEDICAL INSTRUMENT FOR IMPLANTING PINS

The present invention relates to the technical field of devices suitable for implanting pins in long bones in order to restore mechanical strength to said bones.

A particularly advantageous application of the subject matter of the invention lies in treating long bone tumors that affect to a greater or lesser extent the mechanical strength of bones suffering from such tumors.

In the field of orthopedic surgery, various appliances are known for putting cannulated screws into place, e.g. for reducing a fracture by osteosynthesis. In numerous circumstances, and in particular with bones suffering from tumors, implanting screws would appear not to be appropriate given the deterioration in the mechanical strength presented by such bones.

In the field of intervertebral stabilization, Document U.S. 2008/0033432 describes a medical instrument comprising a trocar for penetrating into vertebrae, the trocar having a sheath for passing a tube for inserting a curved implantable rod. The implantable rod is removably mounted using a bayonet connection to a control rod that serves initially to extract the implantable rod from the insertion tube and subsequently to separate the control rod from the implantable rod in order to enable it to be removed.

Such equipment does not enable the implantable rod to be positioned correctly. The rod, which is pushed out from the insertion tube, can follow various paths depending on the medium it encounters.

Patent application U.S. 2013/0324997 describes an instrument enabling treatment means to be placed in a vertebra along a curved implantation path. That instrument presents the same drawbacks as the drawbacks of Document U.S. 2008/0033432, insofar as the treatment means are not placed directly in their final position by the instrument.

The object of the present invention is to propose a novel medical instrument designed to make it possible to reestablish the mechanical strength of long bone by implanting pins that are positioned accurately without degrading the mechanical strength of said bone.

In order to achieve such an object, the medical instrument of the invention for putting pins into place in a long bone, each presenting a determined length and a determined diameter.

According to the invention, the medical instrument comprises:
  at least one rectilinear pin presenting a determined length and a determined diameter;
  an insertion trocar comprising a guide sheath presenting a pointed distal end and a proximal grip end, a removal obturator being slidably mounted inside the sheath from its proximal end;
  a guide for a pin the guide comprising a flexible tube presenting an outside diameter less than the inside diameter of the sheath of the trocar to enable it to be inserted in the sheath from its proximal end, after the obturator has been removed, the flexible tube presenting between its distal end and its proximal end a length that is greater than the length of the pin and an inside diameter that is less than the diameter of the pin so as to leave operating clearance enabling the pin to move in translation inside the flexible tube; and
  a positioner for positioning a pin, the positioner comprising an obturator possessing an outside diameter less than the inside diameter of the flexible tube in order to enable it to be inserted in and to slide inside the flexible tube, the obturator presenting a distal end forming a thrust surface for the pin in order to position the distal end of the pin at the distal end of the flexible tube, the obturator externally defining a guide surface for the flexible tube over a length not less than the length of the flexible tube.

Furthermore, the medical instrument of the invention may also present in combination at least one and/or more of the following additional characteristics:
  the obturator of the positioner defines externally a guide surface for the flexible tube over a length equal to the length of the flexible tube;
  the obturator of the positioner is fitted with an indicator that is slidably mounted on the obturator to identify the degree to which the obturator is pushed into the inside of the flexible tube in order to position the distal end of the pin at the distal end of the flexible tube;
  the guide surface of the obturator possesses a length between the indicator and the proximal end that is equal at least to the length of a pin;
  the obturator of the positioner is fitted as an indicator with a mark or with a cursor slidably mounted on the obturator to identify the degree to which the obturator is pushed into the inside of the flexible tube in order to position the distal end of the pin at the distal end of the flexible tube while being put into abutment against the proximal end of the flexible tube;
  the flexible tube is made of a malleable material and the inside diameter of the flexible tube and the diameter of the pin lie in the range 0.5 millimeters (mm) to 2 mm;
  the obturator of the positioner is provided at the proximal end of the guide surface with a stop abutment for the flexible tube;
  the guide for a pin includes a bearing cross-bar removably mounted on the guide in order to release access to the proximal end of the flexible tube;
  each pin is provided with a distal end and with a proximal end that are defined by at least three facets of different orientations that come together at a blunted end portion; and
  the sheath of the trocar presents a distal end with a beveled face terminated in a point.

Another object of the invention is to propose a novel method of treating long bone tumors by implanting pins from an epiphysis of the bone in order to improve its mechanical strength without degrading it natural strength, such pins advantageously being embedded in a cement.

In order to achieve such an object, the method of putting pins into place inside a long bone using an instrument of the invention comprises the following steps for putting a pin into place:
  from an epiphysis of the bone, putting a trocar into place, the trocar comprising a guide sheath in which an obturator is slidably mounted;
  after removing the obturator from the trocar, inserting a guide for a pin into the proximal end of the guide sheath, the guide comprising a flexible tube having its distal end positioned at the point where the distal end of the pin is to be implanted;
  inserting a pin and then a positioner for a pin into the flexible tube from its proximal end, the positioner comprising an obturator that is moved so as to bring the distal end of the pin to the distal end of the flexible tube;
  maintaining the pin positioner in a stationary position while simultaneously exerting traction on the guide in order to withdraw the guide from the pin; and
  removing the guide, the positioner, and the trocar.

Furthermore, the method of the invention may also consist in combining at least one or more of the following additional characteristics:
- putting an indicator into place on the obturator of the positioner in such a manner that the distal end of the pin is situated at the distal end of the guide when the indicator is situated at the proximal end of the guide;
- for the purpose of putting another pin into place, implanting a trocar in the epiphysis of the bone along an implantation direction that is different from the first implantation, and in repeating the steps for putting a pin into place; and
- injecting a cement into the bone, the cement being inserted into the guide and being put into place using the obturator of the positioner.

Other characteristics and advantages appear from the following description made with reference to the accompanying drawings, which show embodiments of the invention as non-limiting examples.

FIG. 1 is a face view of an insertion trocar forming part of the medical instrument in accordance with the invention.

FIGS. 1A and 1B are respectively a profile view and a back view of the trocar shown in FIG. 1.

FIG. 10 is a view showing the introduction of an obturator of a positioner for a pin in the pin guide.

FIG. 11 is a view showing a pin being put into place in the bone by removal of the pin guide.

Figure 2:
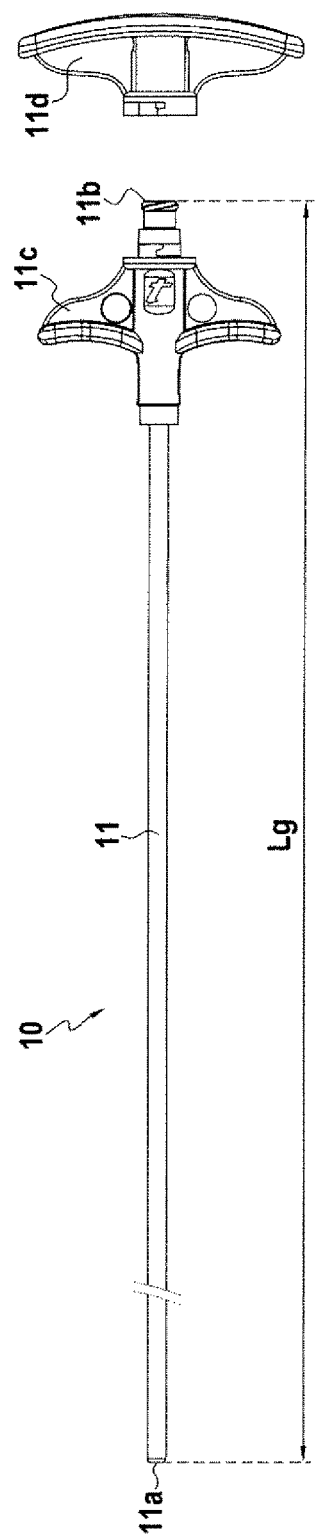
FIG. 2 is a view of a guide for a pin forming part of the medical instrument in accordance with the invention.
Figure 3:
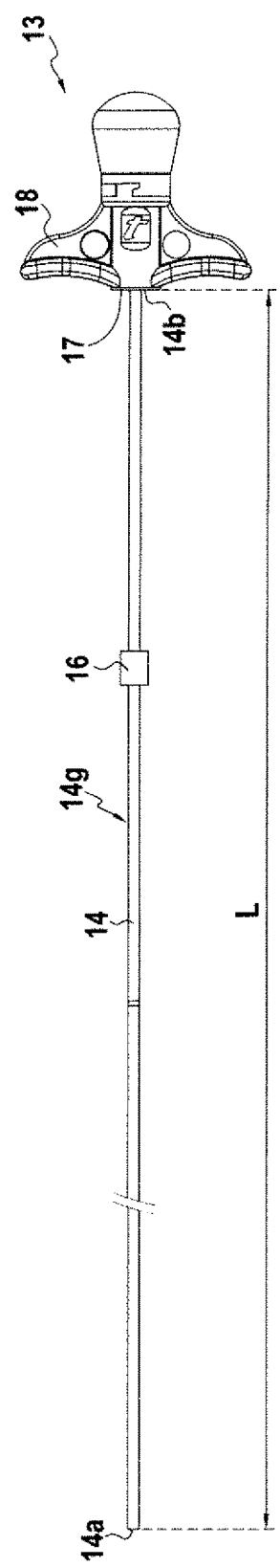
FIG. 3 is a view of a pin positioner forming part of the medical instrument in accordance with the invention.
Figure 4:
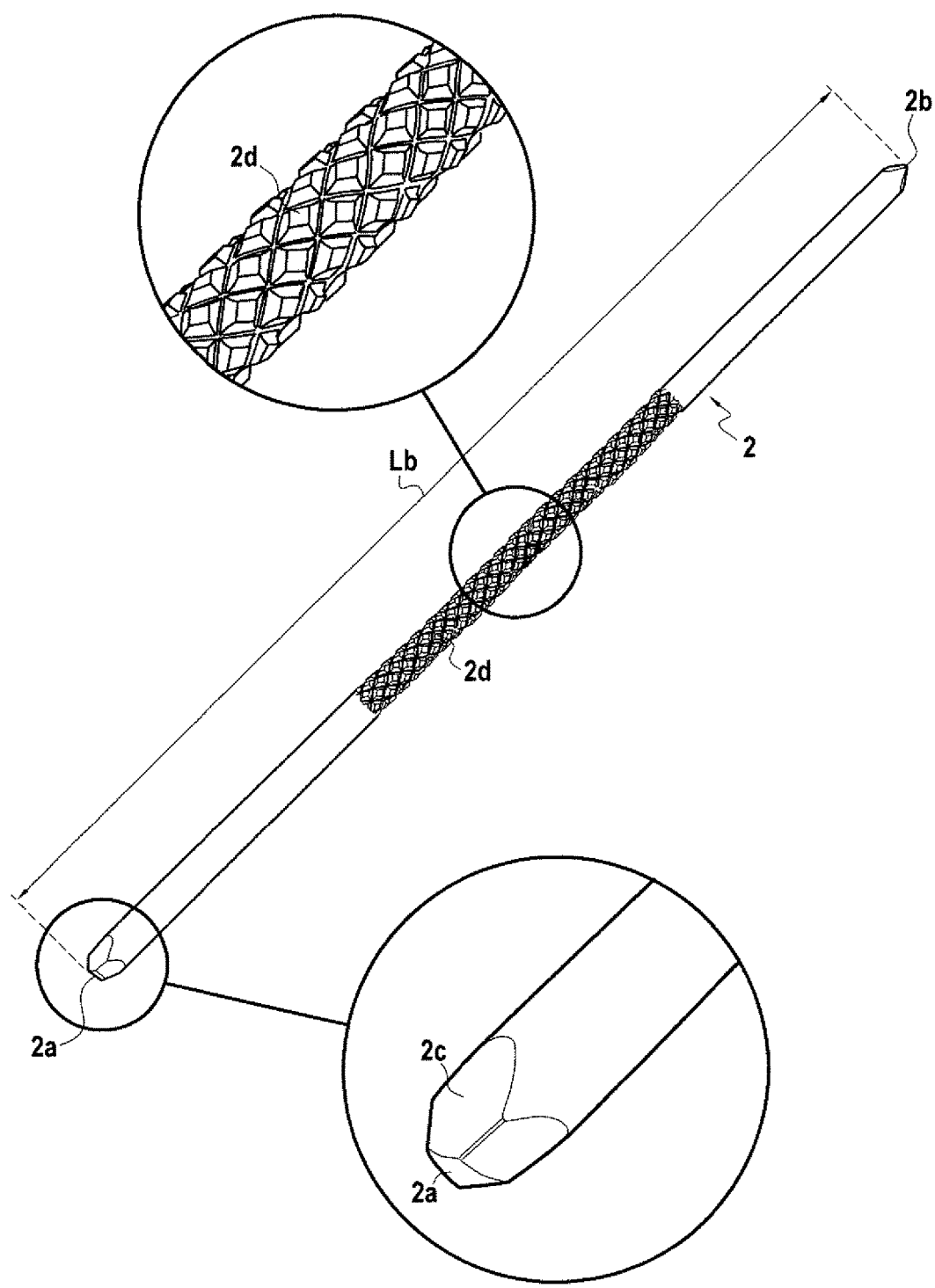
FIG. 4 is a view of a pin forming part of the medical instrument in accordance with the invention.

As can be seen from FIGS. 1 to 4, the subject matter of the invention relates to a medical instrument 1 for putting at least one and more generally a plurality of pins 2 into place in a long bone 3, such as for example the femur, the tibia, the radius, or the ulna. Each pin 2 presents between a distal end 2$a$ and a proximal end 2$b$, a determined length Lb lying in the range 5 centimeters (cm) to 25 cm, that is selected to be appropriate for reconstructing the mechanical strength of the bone (FIG. 4). Each pin 2 is straight or rectilinear and possesses a diameter lying in the range 2 mm to 5 mm that is selected to correspond to the mechanical strength of the reconstruction. The pins 2 may be made of any medical-grade material that is implantable in the human body.

Advantageously, each of the distal and proximal ends 2$a$ and 2$b$ of the pins has at least three facets 2$c$ of different orientations that come together at a common end portion that is blunt or rounded. Advantageously, each facet 2$c$ is at an angle lying in the range 15° to 45° relative to the longitudinal axis of the pin, while the common end portion presents a minimum radius of curvature that is greater than or equal to 1 mm. Such a configuration for the ends of the pins 2 enables the pins to slide over one another when multiple pins are being implanted, as explained in the description below. In an advantageous embodiment, each pin 2 has a central portion 2$d$ with surface treatment to give it roughness that is appropriate for holding the pin in a mass of cement.

Figure 5:
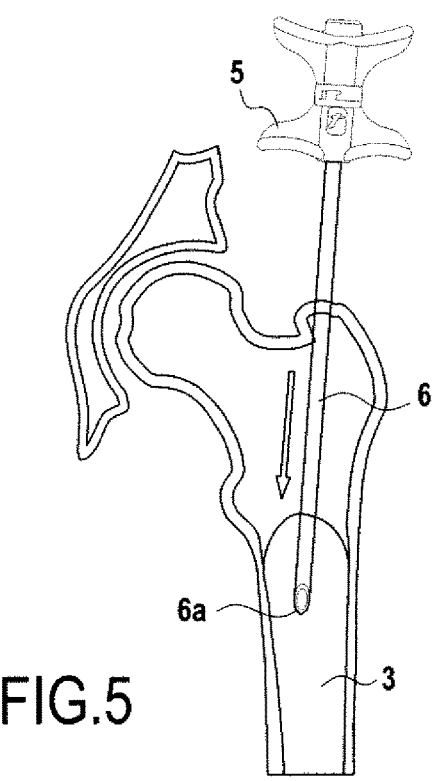
FIG. 5 is a view showing an insertion trocar forming part of the medical instrument in accordance with the invention being put into place.
Figure 6:
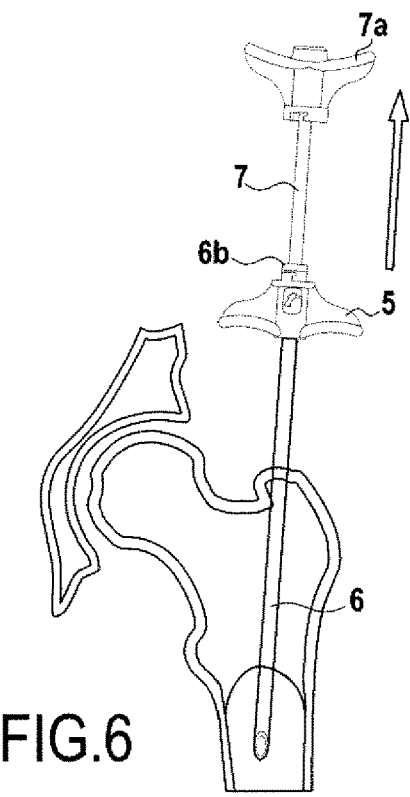
FIG. 6 is a view showing the removal of the obturator of the insertion trocar forming part of the medical instrument in accordance with the invention.

The medical instrument 1 also comprises an insertion trocar 5 comprising a guide sheath 6 having a pointed distal end 6$a$, preferably in the form of a beveled tip so as to present great penetration power into bone (FIGS. 1, 5, and 6).

As can be seen more clearly in FIGS. 1, 1A, and 1B, the distal end 6$a$ of the sheath 6 of the trocar 5 presents a beveled face $6_1$ with an anterior portion $6_2$ that is pointed. Advantageously, the beveled face $6_1$ extends from the anterior portion $6_2$ at an angle a of about 30° relative to the axis of the sheath 6. The beveled face $6_1$ preferably extends away from the anterior portion $6_2$ at an angle b that is less than the angle a (e.g. about 25°). The distal end 6$a$ of the sheath 6 preferably has two beveled facets $6_3$ on its side opposite to the beveled face $6_1$, the beveled facets $6_3$ coming together at the pointed anterior portion $6_2$.

The guide sheath 6 at its end opposite from the distal end 6$a$ has a proximal grip end 6$b$ fitted with a bearing body 6$c$ against which the fingers can bear, which body extends transversely on either side of the sheath 6. The trocar 5 also has an obturator 7 slidably mounted inside the sheath 6, starting from its proximal end 6$b$. Conventionally, the obturator 7 is removable from the guide sheath 6 and it is provided at its proximal end with a grip cross-bar 7$a$. When the obturator 7 is withdrawn from the sheath 6, then the proximal end 6$b$ of the sheath is disengaged.

The medical instrument 1 also has a guide 10 for a pin 2, the guide comprising a flexible tube 11 having an outside diameter that is smaller than the inside diameter of the sheath 6 of the trocar so as to enable it to be inserted into the sheath 6 from its proximal end 6$b$, naturally after removing the obturator 7 from the trocar. The flexible tube 11 is made of a malleable material such as a metal alloy, e.g. a stainless steel or a hyper-quenched composite steel. As explained below in the description, the flexible tube 11 is malleable in the sense that the tube is deformable and suitable for conserving the deformed shape it takes on.

The flexible tube 11 possesses a distal end 11$a$, e.g. a straight end for identification purposes while putting pins into place, as explained in the description below. Between its distal end 11$a$ and its proximal end 11$b$, the flexible tube 11 has a length Lg that is greater than the length Lb of the pin and an inside diameter that is greater than the diameter of the pin in order to present operating clearance that allows the pin to move in translation inside the flexible tube 11. Advantageously, the difference between the inside diameter of the flexible tube 11 and the diameter of the pin 2, i.e. the operating clearance, lies in the range 0.5 mm to 2 mm.

Advantageously, the flexible tube 11 has a bearing body 11$c$ at its proximal end 11$b$ against which the fingers can be pressed and having removably mounted thereon a bearing cross-bar 11$d$ that, on being removed, serves to release access to the proximal end 11$b$ on the flexible tube 11.

The medical instrument 1 also has a positioner 13 for a pin 2, the positioner comprising an obturator 14 possessing an outside diameter less than the inside diameter of the flexible tube 11 so as to be capable of being inserted into the flexible tube 11 and of being slid therealong in order to position the distal end 2$a$ of the pin 2 at the distal end 11$a$ of the flexible tube. The obturator 14 has a distal end 14$a$ forming a thrust surface for the pin 2.

According to a characteristic of the invention, the obturator 14 of the positioner 13 defines externally a guide surface 14g for the flexible tube 11 when the guide 10 is to be removed after the pin 2 has been put finally into position. This guide surface 14g of the obturator 14 of the positioner 13 possesses a length L that is not less than the length of a pin 2. The length L of the guide surface 14g is taken between the distal end 14a of the obturator 14 of the positioner 13 and its proximal end 14b.

In an advantageous embodiment variant, the obturator 14 of the positioner 13 defines externally a guide surface 14g for the flexible tube over a length L that is substantially equal to the length Lb of the flexible tube 11. Specifically, when the obturator 14 of the positioner 13 has placed the distal end 2a of the pin at the distal end of the flexible tube 11, then the obturator 14 penetrates inside the flexible tube over a length equal to the length Lg of the flexible tube 11 minus the length Lb of the pin. Outside the flexible tube 11, the obturator 14 needs to present a guide surface 14g of length that is not less than the length Lb of the pin so as to enable the flexible tube 11 to be disengaged relative to the pin 2.

In a preferred embodiment variant, the obturator 14 of the positioner 13 is fitted with an indicator 16 for indicating the degree to which the obturator 14 of the positioner 13 has been pushed into the inside of the flexible tube 11 in order to position the distal end 2a of the pin 2 at the distal end 11a of the flexible tube. This indicator 16 may be formed by a sign or a mark made on the obturator 14 or it may be formed by a cursor slidably mounted on the obturator so as to enable the degree to which the obturator is pushed in to be adjusted. The indicator 16 is preferably made or mounted so as to be positioned at the proximal end 11b of the guide 10 when the obturator 14a has positioned the distal end 2a of the pin at the distal end 11a of the flexible tube 11.

In the example shown in the drawings, the indicator 16 is a cursor that is slidably mounted on the obturator 14 in order to identify the degree to which the obturator has been pushed into the flexible tube 11 in order to position the distal end 2a of the pin 2 at the distal end 11a of the flexible tube on coming into abutment against the proximal end 11b of the flexible tube 11. As explained in the description below, the cursor 16 is moved in translation by the guide 10 during the operation of removing it.

Advantageously, the obturator 14 of the positioner is provided at the proximal end 14b of the guide surface 14 with a stop abutment 17 for the flexible tube 11. For example, the stop abutment 17 may be made on a grip handle 18 fitted to the obturator 14. When the positioner 13 is provided with a cursor 16 that is slidably mounted on the obturator 14 of the positioner 13, then the length L of the guide surface 14g is taken between the distal end 14a of the obturator 14 of the positioner 13 and the cursor 16 occupying its position in abutment against the stop abutment 17.

In other words, the distance between the indicator for indicating the degree of pushing in and the proximal end 14b of the obturator, i.e. the stop abutment 17, is equal to not less than the length Lb of a pin 2, and is preferably to the length of a pin 2.

Use of the medical instrument 1 of the invention stems directly from the above description.

The medical instrument 1 of the invention serves to put at least one pin 2 into place in a tumor zone T affecting the femur bone 3 in the example shown in FIGS. 5 to 11 that describe steps of use. The first step consists in putting the trocar 5 into place from an epiphysis of the bone. The approach is along the axis of the long bone from one of its epiphyses. This approach is transcutaneous and guided by X-rays. The trocar 5 penetrates into the bone passing through the bone barrier so that the distal end 6a of the trocar 5 reaches the medullary cavity of the bone (FIG. 5).

The obturator 7 of the trocar 5 is then removed, as shown in FIG. 6.

Figure 7:
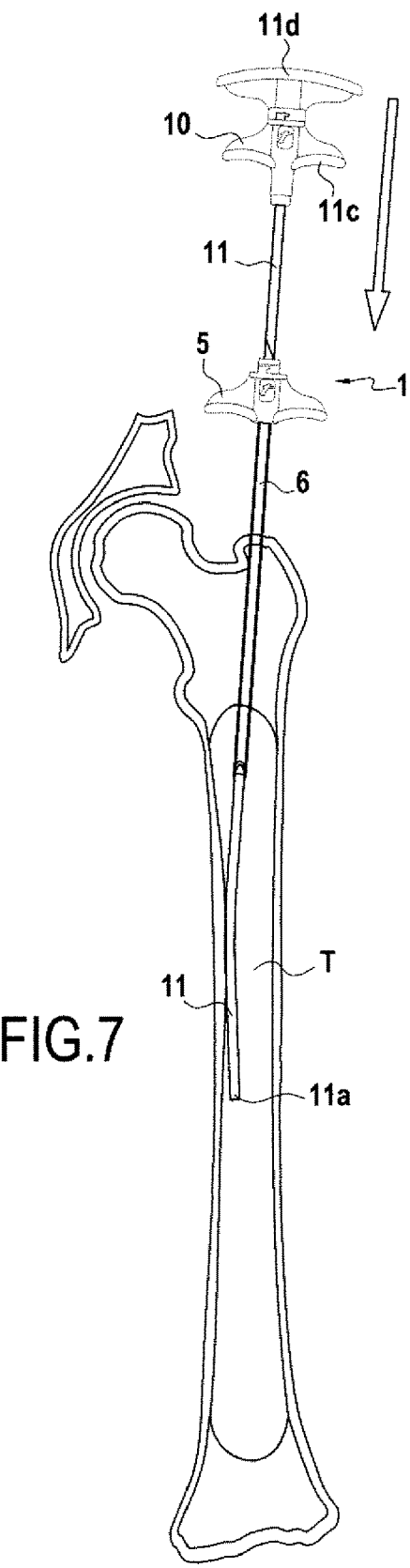
FIG. 7 is a view showing the pin guide being put into place in the insertion trocar.

Thereafter, the guide 10 is inserted into the trocar 5 by inserting the distal end 11a of the flexible tube into the guide sheath 6 so that the distal end 11a of the flexible tube 11 is positioned at the point for implantation of the distal end of the pin (FIG. 7). It should be observed that the flexibility of the flexible tube 11 makes it possible to follow the path imposed by the internal cortex of the bone. In other words, because of the malleable nature of the flexible tube 11, it complies with the more or less sinuous path imposed by the internal cortex of the bone. The final position of the distal end 11a of the flexible tube 11 is obtained by X-ray imagery. It should be observed that if the distal end 11a of the flexible tube 11 does not occupy the position desired for the distal end of the pin 2, then the guide 10 is manipulated once more, e.g. along a different path in order to cause the distal end 11a of the flexible tube to occupy the desired position.

Figure 8:
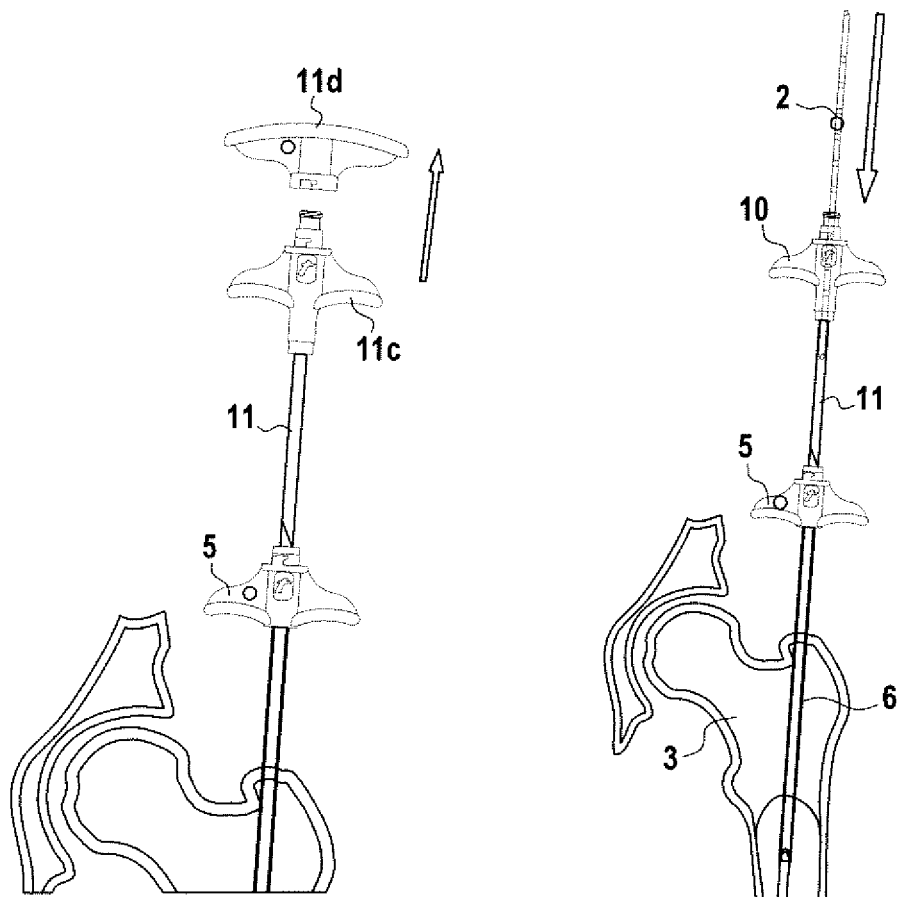
FIG. 8 is a view showing the removal of the cross-bar of the pin guide.
Figure 9:
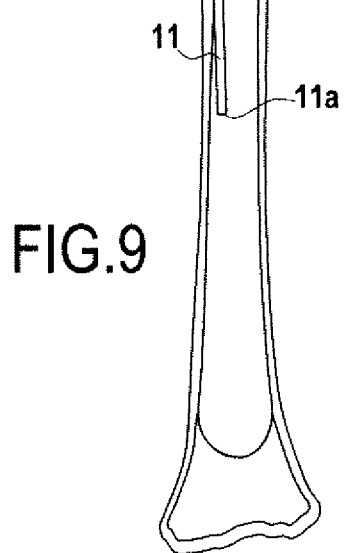
FIG. 9 is a view showing a pin being put into place in the pin guide.

Thereafter, the method consists in removing the thrust cross-bar 11d so as to release access to the proximal end 11b of the flexible tube (FIG. 8). The method consists in inserting a pin 2 (FIG. 9) into the flexible tube 11 held stationary in position relative to the trocar via the proximal end 11b of the tube and then in inserting the positioner 13 (FIG. 10). The obturator 14 of the positioner 13 is moved inside the flexible tube 11 so as to push against the pin 2 and bring the distal end 2a of the pin 2 to the distal end 11a of the flexible tube 11. When the obturator 14 is fitted with an indicator or a cursor 16, then the indicator or cursor is positioned on the obturator 14 at a distance from the distal end 14a of the obturator that is equal to the length Lg of the flexible tube 11 minus the length Lb of the pin. The obturator 14 is thus pushed so as to move the pin 2 until the indicator 16 is situated at the proximal end 11b of the flexible tube 11 or the cursor 16 comes into abutment against the proximal end 11b of the flexible tube 11. In this abutment position, the penetration stroke of the obturator 14 is stopped since the distal end 2a of the pin 2 coincides with the distal end 11a of the flexible tube 11.

Thereafter, the method consists in keeping the positioner 13 of the pin in a stationary position and simultaneously in exerting traction on the guide 10 so as to remove the flexible tube 11 relative to the pin 2 (FIG. 11). Insofar as the obturator 14 of the positioner 13 is held in a stationary position, the pin 2 stays in position while the flexible tube 11 is being removed relative to the pin 2.

It should be observed that the cursor 16 is mounted on the obturator 14 with the ability to move when subjected to the thrust force from the guide 10 while it is being removed. The cursor 16 thus acts as a brake on the guide 10.

Advantageously, the guide 10 is moved in translation over a stroke equal to the length Lb of the pin. The end of the withdrawal stroke of the guide 10 advantageously corresponds to the proximal end 11b of the flexible tube coming into abutment against the stop abutment 17. Specifically, the guide surface 14g of the obturator 14 possesses a length between the indicator 16 and the proximal end 14b of the obturator fitted with the stop abutment 17 that is equal to the length of a pin 2.

Finally, the guide 10, the positioner 13, and the trocar 5 are withdrawn. The method of the invention as described above is advantageously repeated to implant a new pin 2 in the tumor zone T. For this purpose, the trocar 5 is inserted into the epiphysis of the bone along an implantation direction that is different from the direction of the first implantation. The above-described steps for putting a pin into place are then repeated. A plurality of pins 2 can thus be implanted in the form of a bundle for improving the mechanical strength of the bone. The facetted shape of the distal ends of the pins enables them to slide over one another while eliminating any risk of the pins pushing against one another.

After the pins 2 have been implanted, the method consists in injecting cement into the bone, which cement is inserted into the guide 10 and put into place using the obturator 14 of the positioner 13. The pins 2 are thus embedded in a cement that consolidates the long bone.

The invention is not limited to the examples described and shown since various modifications may be made thereto without going beyond the ambit of the invention.

The invention claimed is:

1. A medical instrument for putting at least one rectilinear pin (2) of a determined length and a determined diameter (2) into place in a long bone (3), the medical instrument comprising:
    an insertion trocar (5) comprising a guide sheath (6) presenting a pointed distal end (6a) and a proximal grip end, a removable obturator (7) being slidably mounted inside the guide sheath from a proximal end thereof;
    a guide (10) for the at least one rectilinear pin (2), the guide comprising a flexible tube (11) presenting an outside diameter less than an inside diameter of the guide sheath of the insertion trocar to enable the flexible tube to be inserted in the guide sheath from the proximal end thereof, after the removable obturator has been removed, the flexible tube (11) presenting between a distal end and a proximal end thereof a length that is greater than the determined length of the at least one rectilinear pin and an inside diameter that is greater than the determined diameter of the pin so as to leave operating clearance enabling the at least one rectilinear pin to move in translation inside the flexible tube; and
    a positioner (13) for positioning the at least one rectilinear pin (2), the positioner comprising a positioner obturator (14) possessing an outside diameter less than the inside diameter of the flexible tube (11) in order to enable the positioner obturator to be inserted in and to slide inside the flexible tube, the positioner obturator (14) presenting a distal end (14a) forming a thrust surface for the at least one rectilinear pin (2) in order to position the distal end of the at least one rectilinear pin at the distal end of the flexible tube, the positioner obturator (14) externally defining a surface (14g) for the flexible tube (11) over a length not less than the length of the flexible tube.

2. The instrument according to claim 1, characterized in that the positioner obturator (14) defines externally the surface (14g) for the flexible tube over a length equal to the length of the flexible tube.

3. The instrument according to claim 1, characterized in that the positioner obturator (14) is fitted with an indicator (16) to identify a degree to which the positioner obturator is pushed into the inside of the flexible tube (11) in order to indicate a position of a distal end (2a) of the at least one rectilinear pin (2) at the distal end (11a) of the flexible tube (11).

4. The according to claim 3, characterized in that the surface (14g) of the positioner obturator possesses a length between the indicator (16) and a proximal end (14b) of the positioner obturator that is equal at least to the length (Lb) of the at least one rectilinear pin (2).

5. The instrument according to claim 3, characterized in that the indicator (16) has a mark or a cursor and is slidably mounted on the positioner obturator to identify the degree to which the positioner obturator is pushed into the inside of the flexible tube (11) in order to position the distal end (2a) of the at least one rectilinear pin (2) at the distal end (11a) of the flexible tube (11) while being put into abutment against the proximal end (11b) of the flexible tube (11).

6. The instrument according to claim 1, characterized in that the flexible tube (11) is made of a malleable material and in that the inside diameter of the flexible tube (11) and the determined diameter of the at least one rectilinear pin (2) lie in the range 0.5 mm to 2 mm.

7. The instrument according to claim 1, characterized in that the positioner obturator (14) is provided at the proximal end of the surface with a stop abutment (17).

8. The instrument according to claim 1, characterized in that the guide (10) for the at least one rectilinear pin (2) includes a bearing cross-bar (11d) removably mounted on the guide in order to allow access to the proximal end (11b) of the flexible tube.

9. A medical instrument system comprising the medical instrument according to claim 1 and the at least one rectilinear pin, characterized in that the at least one rectilinear pin (2) is provided with a distal end (2a) and with a proximal end (2b) that are defined by at least three facets of different orientations that come together at a blunted end portion.

10. The instrument according to claim 1, characterized in that the guide sheath (6) of the insertion trocar (5) comprises a distal end (6a) with a beveled face terminated in a point.

11. A method of putting at least one rectilinear pin (2) into place inside a long bone (3) using an instrument according to claim 1, the method for putting the at least one rectilinear pin (2) into place comprising:
    from an epiphysis of the bone, putting the insertion trocar (5) into the long bone, the insertion trocar comprising the guide sheath (6) in which the obturator (7) is slidably mounted;
    after removing the obturator (7) from the insertion trocar (5), inserting the guide (10) for the at least one rectilinear pin (2) into the proximal end of the guide sheath (6), the guide comprising the flexible tube (11) having the distal end (11a) thereof positioned at the point where the distal end (2a) of the at least one rectilinear pin (2) is to be implanted;
    inserting the at least one rectilinear pin (2) and then the positioner (13) for the at least one rectilinear pin (2) into the flexible tube (11) from its proximal end, the positioner comprising the positioner obturator (14) that is moved so as to bring the distal end (2a) of the at least one rectilinear pin (2) to the distal end (11a) of the flexible tube (11);
    maintaining the positioner (13) in a stationary position while simultaneously exerting traction on the guide (10) in order to withdraw the guide from the at least one rectilinear pin; and
    removing the guide (10), the positioner (13), and the insertion trocar (5) from the long bone.

12. The method according to claim 11, comprising putting an indicator (16) into place on the positioner obturator (14) in such a manner that the distal end (2a) of the at least one rectilinear pin (2) is situated at the distal end (11a) of the guide (10) when the indicator (16) is situated at the proximal end (11b) of the guide (10).

13. The method according to claim 11, wherein for the purpose of putting another rectilinear pin (2) into place, the insertion trocar (5) is implanted in the epiphysis of the bone (3) along an implantation direction that is different from a first implantation direction in the long bone, and then repeating the steps of putting, removing, inserting the guide, and inserting the other rectilinear pin into place.

14. The method according to claim 11, comprising injecting a cement into the bone, the cement being inserted into the guide (10) and being put into the bone using the positioner obturator (14) of the positioner (13).

* * * * *